United States Patent [19]

Taylor

[11] Patent Number: 4,887,615
[45] Date of Patent: Dec. 19, 1989

[54] STERILE DRAPE FOR ULTRASOUND PROBE

[75] Inventor: Richard H. Taylor, Columbus, Miss.

[73] Assignee: Microtek Medical Inc., Columbus, Miss.

[21] Appl. No.: 291,111

[22] Filed: Dec. 28, 1988

[51] Int. Cl.$^4$ .............................................. A61F 13/00
[52] U.S. Cl. ................................... 128/850; 128/856; 128/844
[58] Field of Search ............... 128/849, 846, 850, 856, 128/844; 604/347

[56] References Cited

U.S. PATENT DOCUMENTS

| | | | |
|---|---|---|---|
| 1,196,250 | 8/1916 | Kuhn | 128/850 |
| 1,351,917 | 9/1920 | Kuhn | 128/850 |
| 2,305,453 | 12/1942 | Martos | 128/846 |
| 2,348,773 | 5/1944 | Wyman | 2/21 |
| 3,968,792 | 7/1976 | Small | 128/856 |
| 4,119,093 | 10/1978 | Goodman | 128/856 |
| 4,781,709 | 11/1988 | Grubman | 604/349 |
| 4,794,920 | 1/1989 | Robichaud | 128/844 |

*Primary Examiner*—Robert A. Hafer
*Assistant Examiner*—Lynda M. Cofsky
*Attorney, Agent, or Firm*—Antonelli, Terry & Wands

[57] ABSTRACT

A sterilizable drape for draping an ultrasound probe during an invasive ultrasonographic procedure, and a process of forming such a drape. An elongated sleeve member, having an open first end and a substantially closed second end with a circular fenestration therethrough, is formed of a sterilizable, flexible, fluid impervious material such as polyethylene. A pair of pull ties extend from the open end to aid in pulling the drape over an ultrasound probe and cable. A tubular member, having an outside diameter substantially equal to the fenestration diameter and formed of a sterilizable, flexible, resilient, fluid impervious material such as latex, is sealed to the sleeve member and extends through the fenestration. The tubular member has an open first end, communicating with the sleeve member interior through the fenestration, and a closed second end. To form the drape, a circular fenestration is formed through substantially the center of a rectangular piece of sterilizable, flexible, fluid impervious material. The tubular member is inserted through the fenestration and sealed to the rectangular piece by a two-sided tape. Longitudinally extending slits are formed at diametrically opposite sides of an open ended sleeve of the same fluid impervious material, and the ends of the rectangular piece are heat sealed to the folded back sleeve side walls. Each folded over side of the rectangle is heat sealed to itself so that the rectangular piece forms an extension of the sleeve. The pull tabs are added, and the drape is accordian folded and sterilized.

30 Claims, 1 Drawing Sheet

STERILE DRAPE FOR ULTRASOUND PROBE

BACKGROUND OF THE INVENTION

The present invention pertains to a sterile drape for hospital use. More particularly, the present invention pertains to a sterile drape for an ultrasound probe used in invasive ultrasound procedures such as ovum retrieval for in vitro fertilization, various cardiovascular procedures, and various neurosurgical procedures.

Invasive ultrasound procedures are carried out in various situations. Some cardiovascular and neurosurgical procedures include invasive ultrasonic examinations. By way of further example, a woman desiring to undergo in vitro fertilization may be given a vaginal ultrasound examination prior to the procedure in order to monitor the follicular development. Once the follicles have reached the appropriate size, an ultrasonographic ovum retrieval procedure may be performed to obtain ova for fertilization. Subsequently, the fertilized ova may be returned to the uterus utilizing an ultrasonographic procedure.

The ultrasound probe is enclosed in a disposable sterile enclosure during the invasive ultrasonic procedure. One type of ultrasound probe used in invasive procedures may have a length in the order of about two inches and a diameter in the order of about one and a half inches. Another type may have a length in the order of about three and a half inches and a diameter in the order of about one-half inch. With either probe, the probe extends from an elongated cable attached to ultrasonographic equipment. The probe and the adjacent length of the cable must be within a sterile enclosure to assure aseptic conditions.

Suitable enclosures have not been available for ultrasound probes. A commonly used technique has been to place a television camera drape over the cable and a condom over the probe, and then to tape the condom to the end of the drape. See, for example, the paper "Ultrasonographic Transvaginal Ovum Retrieval, A New Approach To In Vitro Fertilization," by Florence Greennan Rabar, RN; Cheryl Oppenheim Falksom, RN; and Barbara Morten-Stella, RN, *Association of Operating Room Nurses Journal,* Vol. 48, No. 1, page 36 et seq., July 1988. Such techniques have not been altogether satisfactory, however. The placement of the television camera drape over the cable and then the placement of the condom over the probe and taping of the condom to the drape is an awkward, time consuming procedure. If the probe or cable contact the exterior of the condom or the drape, sterility is compromised. Additionally, if the taped function of the condom and the drape is not completely sealed, sterility cannot be assured. Further, any corners or other protrusions from the drape can injure the patient.

SUMMARY OF THE INVENTION

The present invention is a sterile drape for enclosing an ultrasound probe to assure sterility during invasive ultrasound procedures. The drape in accordance with the present invention includes an elongated sleeve member formed of a sterilizable, flexible, fluid impervious material with an open first end and a substantially closed second end having a circular fenestration therethrough. A tubular member having an open first end, a closed second end and a diameter substantially equal to the diameter of the sleeve member fenestration extends from and is sealingly fastened to the substantially closed end of the sleeve member, with the tubular member open end communicating with the sleeve interior through the sleeve member fenestration.

The present invention is also a process of forming such a drape. In accordance with the process, a circular fenestration is formed through substantially the center of a rectangular piece of sterilizable, flexible, fluid impervious material. A toroidal shaped piece of doubled sided tape is attached to the rectangular piece of material, encircling the fenestration. A tubular member, having an outside diameter substantially equal to the diameter of the fenestration, an open first end, and a closed second end and formed of a sterilizable, flexible, resilient, fluid impervious material is inserted through the fenestration and sealed to the second side of the tape. The first end of the tubular member is attached to the tape, sealing the tubular member to the rectangular material. A relatively short, longitudinally extending slit is formed in diametrically opposite sides of an elongated, open-ended sleeve member formed of a sterilizable flexible, fluid impervious material to permit the two opposite sleeve walls to be folded open over the length of the slit. A first end of the rectangular material is attached to one of the folded open sleeve walls, and the opposite end of the rectangular material is attached to the other of the folded open sleeve walls, with the tubular member extending away from the sleeve member. Each side of the rectangular piece of material is sealed to itself so that the rectangular piece of material forms an extension of the sleeve member, with the tubular member extending away from the sleeve member. Pull ties are added to the open end of the sleeve member, and the drape is then sterilized and telescopically folded for packaging and shipment.

When the sterile drape is to be used to drape an ultrasound probe, a conductive gel is preferably utilized to couple the probe to the interior surface of the tubular member, assuring good conduction of the ultrasound signals. By way of example, ULTRA/PHONIC Conductivity Gel, available from Pharmaceutical Innovations, Inc. of Newark, New Jersey might be used. The sterilized ultrasound drape is removed from its package, such a gel is inserted within the tubular member, and the drape is then positioned over the ultrasound probe with the probe inserted within the tubular member. The pull ties are then grasped, and the elongated sleeve member is pulled over the cable of the ultrasound probe. The ultrasographic procedure is then carried out. After the procedure is completed, the drape is removed from the ultrasound probe and discarded.

BRIEF DESCRIPTION OF THE DRAWINGS

These and other aspects and advantages of the present invention are more apparent from the following detailed description and claims, particularly when considered in conjunction with the accompanying drawings. In the drawings:

DETAILED DESCRIPTION OF A PREFERRED EMBODIMENT

Figure 1:
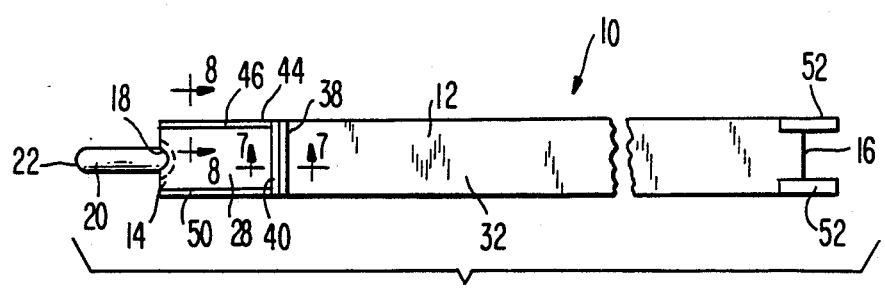
FIG. 1 is a broken elevational view of a preferred embodiment of an ultrasound probe drape in accordance with the present invention.

FIG. 1 depicts a completed ultrasound probe drape 10 in accordance with a preferred embodiment of the present invention. Drape 10 includes an elongated sleeve member 12 with an open first end 16 and a substantially closed second end 14. A circular fenestration 18 is provided in second end 14, and a tubular member 20 extends through fenestration 18. Tubular member 20 has a diameter substantially equal to the diameter of fenestration 18.

Figure 2:
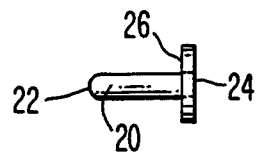
FIG. 2 is an elevational view of a flexible, resilient, fluid impervious tubular member suitable for incorporation into the ultrasound probe drape of FIG. 1 in accordance with the present invention.

As depicted in FIG. 2, tubular member 20 has an open first end 24 and a closed second end 22, with an annular flange 26 encircling first end 24. As seen in FIG. 1, closed second end 22 of tubular member 20 extends through fenestration 18 in sleeve member 12, and flange 26 is attached to the inner surface of closed end 14 of the sleeve member.

In the preferred embodiment depicted in FIG. 1, a pair of pull tabs 52 extend from open first end 16 of drape 10 to aid in pulling the drape over an ultrasound probe and cable. Also in the preferred embodiment of FIG. 1, sleeve member 12 is formed of a first portion 28 and a second portion 32 which are joined together, as more fully described below.

Figure 3:
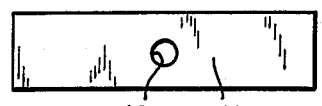
FIG. 3 is a plan view of a rectangular, sterilizable, flexible, fluid impervious material, having a fenestration therein, suitable for incorporation into the ultrasound probe drape of FIG. 1 in accordance with the present invention.
Figure 4:
FIG. 4 is a plan view of toroidal two-sided tape suitable for incorporation into the ultrasound probe drape of FIG. 1 in accordance with the present invention.
Figure 5:
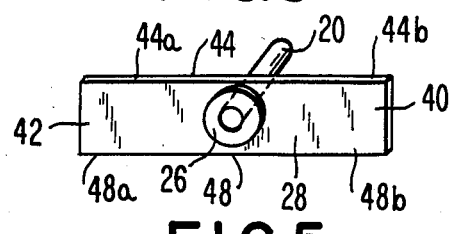
FIG. 5 is a perspective view of the rectangular material of FIG. 3 with the tubular member of FIG. 2 attached thereto by mean of the toroidal tape of FIG. 4.

In the preferred procedure for making drape 10, a circular fenestration 18 is formed in a rectangular piece 28 of sterilizable, flexible, fluid impervious material such as polyethylene, as depicted in FIG. 3. Fenestration 18 can be formed by die cutting, by way of example. Next, as depicted in FIG. 4, a toroidal piece 30 is cut from a two sided tape, for example by die cutting. Toroidal tape piece 30 is then fastened to rectangular piece 28, encircling fenestration 18. Toroidal tape piece 30 can be a two sided tape having medical grade adhesive. Such tapes are commercially available, for example from Minn. Mining & Manufacturing Co. Tubular member 20, depicted in FIG. 2, is then inserted through the opening of toroidal tape 30 and fenestration 18, as depicted in FIG. 5, and flange 26 is pressed against the second side of two sided tape toroid 30, sealing tubular member 20 to rectangular material 28. Tubular member 20 can be made of an elastomeric material such as latex.

Figure 6:
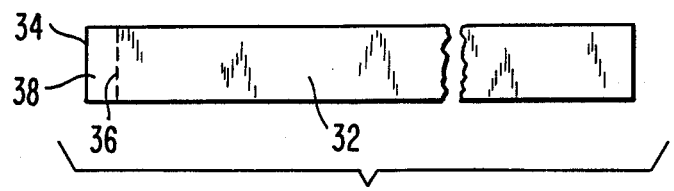
FIG. 6 is a broken elevational view of an elongated sleeve member suitable for incorporation into the ultrasound probe drape of FIG. 1 in accordance with the present invention.
Figure 7:
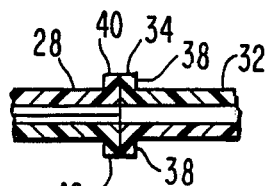
FIG. 7 is a fragmentary sectional view taken along line 7—7 of FIG. 1.
Figure 8:
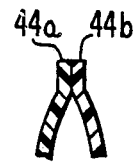
FIG. 8 is a fragmentary sectional view taken along line 8—8 of FIG. 1.

An elongated tubular sleeve member 32, formed of a sterilizable, flexible, fluid impervious material such as polyethylene, is cut to the desired length, as depicted in FIG. 6. Two longitudinally extending slits are formed at diametrically opposite sides of tubular sleeve member 32, with each slit extending from one end 34 of the sleeve member to a point 36. By way of example, sleeve member 32 might have a length in the order of about 83 inches, and each slit might extend in the order of about two inches from end 34 of the sleeve member. If tubular sleeve member 32 is flattened in FIG. 6, then the slits permit two opposite sleeve wall sections 38 to be folded open on a fold line at point 36. A first end 40 (FIG. 5) of the rectangular material 28 is attached to one of the sleeve wall sections 38, for example by heat sealing, and the second end 42 of rectangular material 28 is similarly attached to the second sleeve wall section 38. With rectangular member 28 fastened in this manner to sleeve member 32, first edge 44 of rectangular member 28 is folded over on itself at a fold line passing substantially through fenestration 18. The two halves 44a and 44b of edge 44 are heat sealed together to form a seal 46 (FIG. 1). The second edge 48 of rectangular member 28 is likewise folded over on itself, and the two halves 48a and 48b thereof are heat sealed together to form a seal 50. Material 28, folded, attached to sleeve member 32 and sealed at its sides, thus forms an extension of sleeve member 32.

Figure 9:
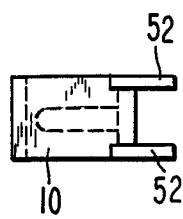
FIG. 9 is an elevational view of the completed drape folded in an accordian fold.

The completed ultrasound probe drape is thus an elongated, sleeve member formed of a sterilizable, flexible, fluid impervious material with an open first end and a substantially closed second end having a circular fenestration therethrough, and a tubular member extending through the fenestration and having a diameter substantially equal to the diameter of the fenestration and formed of a sterilizable, flexible, resilient, fluid impervious material, with an open first end communicating through the fenestration with the interior of the elongated sleeve member and a closed second end, as depicted in FIG. 1. The completed drape 10 can then be sterilized and telescopically folded as depicted in FIG. 9. Pull tabs 52 can be used to pull sleeve member 12 over the cable of an ultrasound probe.

The size of drape 10 depends upon the dimensions of the ultrasound probe to be draped, and so drapes of various sizes might be provided. By way of example, sleeve member 12 might have a circumference in the order of about 10 inches and a length in the order of about 90 inches, although a larger size may be desirable for ease of insertion of conductive gel within tubular member 20. Tubular member 20 preferably has a length in the order of about 6 inches and an outside diameter in the order of about one and three-eighths inches. Thus, fenestration 18 preferably has a diameter in the order of about one and three-eighths inches, and the interior diameter of annular tape piece 30 is likewise in the order of about one and three-eighths inches, while the outside diameter is preferably in the order of about two and one-half inches. Rectangular member 28 preferably has a width in the order of about five inches and a length in the order of about twenty inches. Rectangular member 28 can be formed by utilizing a piece of the tubular material from which sleeve member 32 is cut, splitting that piece into two equal parts longitudinally. Pull tabs 52 are preferably in the order of about four inches long and about eleven-sixteenths inch wide with about a one-half inch wide strip of adhesive extending for a length in the order of about one and one-half inches on one side to permit attachment of the pull tabs to tubular sleeve member 12.

Although the present invention has been described with reference to a preferred embodiment, rearrangements, alterations and substitutions might be made, and still the result would be within the scope of the invention.

What is claimed is:

1. A sterilizable drape for enclosing an ultrasound probe during an ultrasound procedure, said drape comprising:

an elongated sleeve member formed of a sterilizable, flexible, fluid impervious material and including a first elongated tubular portion having open first and second ends and a second portion formed of a rectangular member having a circular fenestration at substantially the center thereof, said second portion being folded longitudinally and having the two longitudinal ends thereof connected to one end of said first portion and having each of the rectangular member sides sealed together to provide an extension of said first member, forming said sleeve member with an open first end and a substantially closed second end with the circular fenestration therethrough; and a tubular member having a diameter substantially equal to the diameter of the fenestration and formed of a sterilizable, flexible, resilient, fluid impervious material, and having an open first end, sealed to said sleeve member second end and communicating with said sleeve member fenestration, and a closed second end.

2. A drape as claimed in claim 1 wherein said first portion and said second portion are formed of a polyethylene material.

3. A drape as claimed in claim 2 wherein said rectangular member longitudinal ends are heat sealed to said one end of said first portion and each of said rectangular member sides is heat sealed together.

4. A drape as claimed in claim 1 wherein said sleeve member has a circumference in the order of about ten inches.

5. A drape as claimed in claim 1 wherein said sleeve member has a length in the order of about 93 inches.

6. A drape as claimed in claim 1 wherein said tubular member is formed of a latex material.

7. A drape as claimed in claim 6 further comprising fastening means sealingly fastening said tubular member to said sleeve member with said tubular member open first end communicating with said tubular member fenestration.

8. A drape as claimed in claim 7 wherein said fastening means comprises a two-sided tape.

9. A drape as claimed in claim 1 wherein said tubular member has a diameter in the order of about one and three-eighths inches.

10. A drape as claimed in claim 1 wherein said tubular member has a length in the order of about six inches.

11. A drape as claimed in claim 1 further comprising a pair of pull tabs attached to said sleeve member adjacent the open first end thereof for pulling said drape over an ultrasonic probe and cable.

12. A process of forming a sterilizable drape for enclosing an ultrasound probe comprising:

forming a circular fenestration through substantially the center of a rectangular piece of sterilizable, flexible, fluid impervious material;

attaching the first side of a piece of double-sided tape on said rectangular piece of material, about the periphery of the fenestration;

inserting through the fenestration a tubular member formed of a sterilizable, flexible, resilient, fluid impervious material and having an outside diameter substantially equal to the diameter of said circular fenestration, an open first end and a closed second end;

attaching said first end of said tubular member to the second side of said double-sided tape, forming a pair of longitudinally extending slits at diametrically opposite sides of a first end of an elongated tubular sleeve member formed of a sterilizable, flexible, fluid impervious material to permit the two opposite sleeve walls to be folded open over the length of the slits;

attaching a first end of said rectangular piece of material to one of said folded open sleeve walls and the opposite end of said rectangular piece of material to the other of said folded open sleeve walls, with said tubular member extending away from said sleeve member; and sealing each side of said rectangular piece of material to itself to form said drape with said rectangular piece of material as an extension of said sleeve member and with said tubular member extending away from said sleeve member.

13. A process as claimed in claim 12 further comprising sterilizing said drape.

14. A process as claimed in claim 12 further comprising telescopically folding said drape.

15. A process as claimed in claim 14 further comprising attaching a pair of pull ties to a second end of said elongated tubular sleeve member before telescopically folding said drape.

16. A process as claimed in claim 15 further comprising sterilizing said drape.

17. A process as claimed in claim 16 further comprising forming said rectangular piece of material by splitting a tubular sleeve of sterilizable, flexible, fluid impervious material.

18. A process as claimed in claim 17 wherein the circular fenestration is formed by die cutting.

19. A process as claimed in 18 further comprising die-cutting a toroidal piece from a piece of two-sided tape material to form the double-sided tape.

20. A process as claimed in claim 19 wherein the first and second ends of said rectangular piece of material are attached to said folded open sleeve walls by heat sealing.

21. A process as claimed in claim 20 wherein each side of said rectangular piece of material is sealed to itself by heat sealing.

22. A process as claimed in claim 12 further comprising attaching a pair of pull tabs to a second end of said elongated tubular sleeve member.

23. A process as claimed in claim 12 further comprising forming said rectangular piece of material by splitting a tubular sleeve of sterilizable, flexible, fluid impervious material.

24. A process as claimed in claim 12 wherein the circular fenestration is formed by die cutting.

25. A process as claimed in claim 12 further comprising die-cutting a toroidal piece from a piece of two-sided tape material to form the double-sided tape.

26. A process as claimed in claim 12 wherein the first and second ends of said rectangular piece of material are attached to said folded open sleeve walls by heat sealing.

27. A process as claimed in claim 34 wherein each side of said rectangular piece of material is sealed to itself by heat sealing.

28. A process as claimed in claim 12 wherein each side of said rectangular piece of material is sealed to itself by heat sealing.

29. A sterilizable drape for enclosing an ultrasound probe during an ultrasound procedure, said drape comprising:
- an elongated sleeve member formed of a sterilizable, flexible, fluid impervious material and having an open first end and a substantially closed second end with a circular fenestration therethrough;
- a tubular member having a diameter substantially equal to the diameter of the fenestration and formed of a sterilizable, flexible, resilient, fluid impervious material, and having an open first end and a closed second end; and
- a two-sided tape having one side thereof affixed to said tubular member first end and the other side thereof affixed to said sleeve member and encircling the fenestration, to sealingly fasten said tubular member to said sleeve member with said tubular member open first end communicating with the interior of said tubular member through the fenestration.

30. A drape as claimed in claim 29 further comprising a pair of pull tabs attached to said sleeve member adjacent the open first end thereof for pulling said drape over an ultrasonic probe and cable.

* * * * *